United States Patent [19]

Malis

[11] Patent Number: 4,813,425
[45] Date of Patent: Mar. 21, 1989

[54] FETAL ELECTRODE PRODUCT

[75] Inventor: Michael J. Malis, Trumbull, Conn.

[73] Assignee: American Home Products Corporation, New York, N.Y.

[21] Appl. No.: 89,528

[22] Filed: Aug. 26, 1987

[51] Int. Cl.⁴ ............................................... A61B 5/04
[52] U.S. Cl. ................................................... 128/642
[58] Field of Search .................. 128/642, 784–786, 128/419 P

[56] References Cited

U.S. PATENT DOCUMENTS

| | | | |
|---|---|---|---|
| 3,827,428 | 8/1974 | Hon et al. | 128/642 |
| 4,682,603 | 7/1987 | Franz | 128/642 |
| 4,686,996 | 8/1987 | Ulbrich | 128/642 |

Primary Examiner—Lee S. Cohen
Attorney, Agent, or Firm—Darby & Darby

[57] ABSTRACT

A fetal electrode product comprises a guide tube, an electrode assembly having a spiral electrode extending from its forward end and a flexible drive tube extending through said guide tube and adapted to engage said electrode assembly for rotating said spiral electrode. The guide tube comprises two relatively rigid sections and an intermediate flexible section such that the curvature of the guide tube can be changed during application of the electrode.

3 Claims, 1 Drawing Sheet

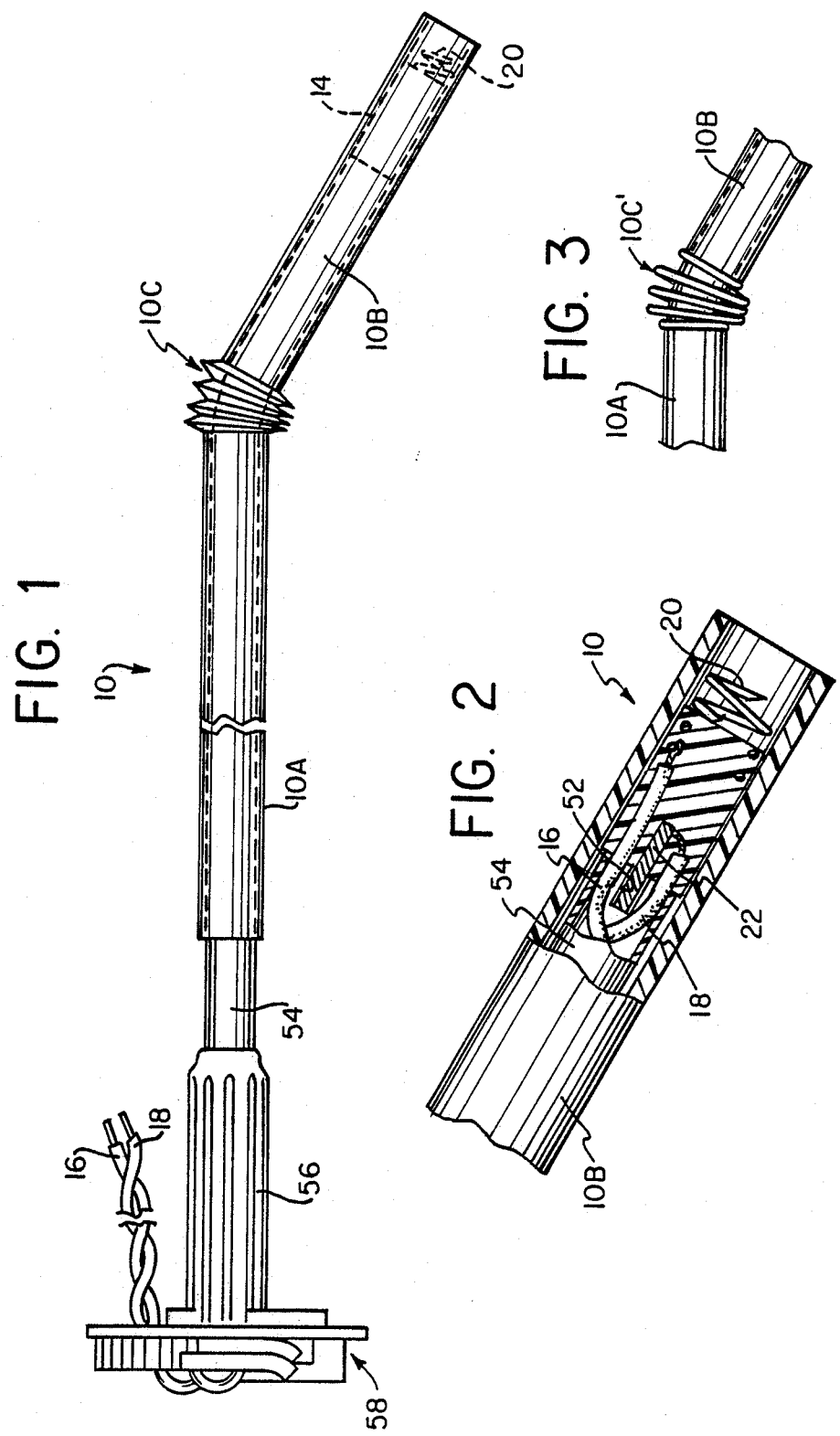

FETAL ELECTRODE PRODUCT

This invention pertains to fetal electrodes. More particularly, this invention relates to an improved guide tube for use with fetal electrodes of the type shown in U.S. Re. Pat. No. 28,990 of Hon et al reissued on Oct. 5, 1976.

BACKGROUND

FIGS. 8–10 of U.S. Re. Pat. No. 28,990 illustrate the fetal electrode most commonly used in the United States today. The product comprises a curved form sustaining guide tube through which an electrode assembly can be delivered to a fetal presenting part (typically the scalp) during delivery. The electrode which engages the fetus is a coil that extends from the forward end of an electrode holder and can be rotated by means of a flexible drive tube passing through the guide tube and adapted to engage a plate-like maternal electrode extending from the rear of the plastic holder.

The device illustrated in the '990 reissue patent has acquired substantial commercial success. The present invention provides an improvement over the guide tube of the '990 reissue patent. Specifically, a guide tube in accordance with the invention helps to ensure proper electrode attachment and is easier to use with an irregularly shaped cervix which may not be readily accommodated by the fixed curve of the guide tube of the '990 reissue patent.

SUMMARY OF THE INVENTION

According to the invention, a guide tube for use with a spiral electrode, wherein a flexible driving tube engages an electrode holder for rotation of the coil electrode, comprises two rigid sections joined by an intermediate flexible section, for example, of a bellows-type or spring construction.

THE DRAWINGS

FIG. 1 is a side elevational view, partially in section, showing the invention;

FIG. 2 is a sectional view showing the configuration of the electrode assembly, and FIG. 3 is a side elevational view, showing an intermediate flexible section as a spring.

DETAILED DESCRIPTION

A guide tube constructed in accordance with the invention can be used with electrodes other than the spiral electrode shown in the '990 patent; however, since that is the preferred version of the electrode it is illustrated in the drawing.

Referring to the drawing, the electrode product includes a guide tube 10 comprising rigid section 10A and 10B interconnected by a flexible section 10C which, as shown in the drawing, may comprise an elongated bellows. In the preferred embodiment, rigid sections 10A and 10B are relatively straight. Although the dimensions are not critical, it is preferred that section 10B be approximately 3 inches in length of a total length of about 12 inches. Section 10C may be made separately with outwardly extending collars adapted to be press-fit into the adjacent ends of the sections 10A and 10B. Section 10C may also comprise a metal or plastic spring 10C' with its ends captured by sections 10A and 10B. Bellows section 10C may be made of metal or plastic.

Section 10B has an open forward end through which a holder member 14 is adapted to pass.

The holder member 14 has a spiral electrode 20 mounted in its forward end and a flat maternal electrode 22 mounted in its rear end.

The diameter of the cylindrical holder member 14 approximates the inner diameter of guide tube 10. Consequently, the holder member prevents lateral movement of the electrode coil 20 (relative to the guide tube) while the coil is being attached to the fetus. Moreover, the length of the holder member 14 is such that when the spiral electrode 20 extends just beyond the end of the guide tube 10 (for attachment to the fetus), the cylindrical holder member within the guide tube prevents skewing of the coil. These features help to reduce the possibility of injury to the fetus when the electrode is being applied.

A first electrode wire 16 extends through the rear end of the holder member 14 and is electrically connected to the rear end of spiral electrode 20. A second electrode wire 18 also extends through the rear end of holder member 14 and is electrically connected to the forward end of the second electrode 22.

Both electrodes 20 and 22 are preferably constructed of stainless steel and are soldered to their respective electrode wires 16 and 18. The holder member 14 is made of an insulating material, such as plastic, and electrically isolates the electrodes 20 and 22 from one another.

A flexible drive tube 54 is slidably and rotatably disposed in the guide tube 10 for rotating the holder 14 to screw the spiral electrode 20 into a fetal epidermis. The forward end of the drive tube 54 is provided with a pair of slots 52 which are adapted to receive the rearwardly extending portion of the plate electrode 22. When the slots 52 on the forward end of the drive tube 54 engage the plate electrode 22, the holder 14 and spiral electrode 20 may be rotated by rotating the flexible drive tube 54.

A cylindrical grip 56 is attached to he rear of drive tube 54. The electrode wires 16 and 18 extend rearwardly through a releasable wire clamp 58 at the back of the drive tube 54 which extends from the rear portion of the guide tube 12 for connection to a suitable apparatus (not shown) for monitoring fetal heartbeat.

In use, with the spiral electrode 20, holder 14 and plate electrode 22 disposed within the guide tube 10 behind the forward end thereof, the doctor inserts the forward end of the guide tube section 10B through the woman's vagina and cervix until the forward end of the guide tube makes contact with the fetal head (or other portion of the fetus). The doctor then holds the forward end of the guide tube 10B stationary and pushes the rear end of the flexible drive tube 54 forwardly until the spiral electrode 20 makes contact with the fetal epidermis.

When the doctor feels or sees that the spiral electrode 20 has contacted the fetal epidermis, he rotates the flexible drive tube 54 while maintaining the guide tube 10 against the fetal head to screw the spiral electrode 20 into the fetal epidermis.

The invention helps to overcome certain problems due to constraints caused by the fixed curvature of the form-sustaining guide tube of the '990 reissue patent. The flexible section 10C of the guide tube according to the invention permits the user to control the curvature of the guide tube during application of the electrode. This makes it easier for the user to see the fetal presenting part and it has been found also to simplify attachment of the electrode to the fetal presenting part in the case of an irregularly shaped cervix. With the invention, the position of the patient is of less importance in assuring proper application of the electrode and the patient's position therefore is of less significance on the ease of application.

What is claimed is:

1. A fetal electrode product, comprising a guide tube, an electrode assembly having a forward end and spiral electrode extending from said forward end, and a flexible drive tube extending through said guide tube, said drive tube releasably engaging said electrode assembly for rotating said spiral electrode, said guide tube being mechanically free of said drive tube and electrode assembly whereby said guide tube remains stationary when said drive tube and electrode assembly are rotated, said guide tube comprising two relatively rigid sections and an intermediate flexible section such that the curvature of the guide tube can be changed during application of the electrode.

2. An electrode product according to claim 1 wherein said flexible section comprises an elongated bellows.

3. An electrode product according to claim 1 wherein said flexible section comprises a spring.

* * * * *